（12）United States Patent
Luo et al.

(10) Patent No.: US 9,532,761 B2
(45) Date of Patent: Jan. 3, 2017

(54) METHOD AND SYSTEM FOR BONE FRACTURE RISK ASSESSMENT

(71) Applicant: CyberLogic, Inc., New York City, NY (US)

(72) Inventors: Gangming Luo, Middle Village, NY (US); Jonathan J. Kaufman, Brooklyn, NY (US)

(73) Assignee: CyberLogic, Inc., New York City, NY (US)

(*) Notice: Subject to any disclaimer, the term of this patent is extended or adjusted under 35 U.S.C. 154(b) by 122 days.

(21) Appl. No.: 14/595,847

(22) Filed: Jan. 13, 2015

(65) Prior Publication Data

US 2015/0196264 A1 Jul. 16, 2015

Related U.S. Application Data

(60) Provisional application No. 61/927,302, filed on Jan. 14, 2014, provisional application No. 61/927,715, filed on Jan. 15, 2014, provisional application No. 61/928,591, filed on Jan. 17, 2014.

(51) Int. Cl.
*A61B 6/00* (2006.01)
*A61B 5/00* (2006.01)
*A61B 6/03* (2006.01)

(52) U.S. Cl.
CPC ............. *A61B 6/505* (2013.01); *A61B 5/4509* (2013.01); *A61B 5/7275* (2013.01); *A61B 6/482* (2013.01); *A61B 6/5217* (2013.01); *A61B 6/032* (2013.01)

(58) Field of Classification Search
CPC combination set(s) only.
See application file for complete search history.

(56) References Cited

U.S. PATENT DOCUMENTS

| | | | |
|---|---|---|---|
| 7,556,045 B1* | 7/2009 | Recknor | G06F 19/363 128/898 |
| 2007/0208597 A1* | 9/2007 | Recknor | G06F 19/3456 705/3 |
| 2013/0184556 A1* | 7/2013 | Kalvesten | A61B 6/505 600/407 |

OTHER PUBLICATIONS

Carter, Dennis R. et al., "New Approaches for Interpreting Projected Bone Densitometry Data," 7 Journal of Bone and Mineral Research No. 2, pp. 137-145 (1992).
Compston, Juliet E., et al., "Relationship of Weight, Height and Body Mass Index With Fracture Risk at Different Sites in Post-menopausal Women: The Global Longitudinal Study of Osteoporosis in Women (GLOW)," 29 Journal of Bone and Mineral Research No. 9, pp. 487-493 (Feb. 2014).

(Continued)

*Primary Examiner* — Phillip A Johnston
*Assistant Examiner* — Hsien Tsai
(74) *Attorney, Agent, or Firm* — Reising Ethington P.C.

(57) ABSTRACT

A method and system for quantitatively evaluating bone fracture risk in a living being are provided that generate a value for an index indicative of a degree of bone fracture risk. In one embodiment, the method includes the step of acquiring values for a height H, a weight W, and a bone mineral density BMD of the living being. The method further includes the step of calculating a quantitative bone fracture risk index QI associated with the living being in accordance with the formula $QI = H^{\alpha} * W^{\beta} / BMD^{\gamma}$ where $\alpha$, $\beta$, and $\gamma$ are constants selected based on previously obtained data indicative of bone fracture risk.

12 Claims, 3 Drawing Sheets

(56) References Cited

OTHER PUBLICATIONS

Cummings, Steven R. et al., "Does Estimating Volumetric Bone Density of the Femoral Neck Improve the Prediction of Hip Fracture? A Prospective Study," 9 Journal of Bone and Mineral Research No. 2, pp. 1429-1432 (1994).

Sornay-Rendu, Elisabeth et al., "In Obese Postmenopausal Women, Bone Microarchitecture and Strength are Not Commensurate to Greater Body Weight: The Os des Femmes de Lyon (OFELY) Study," 28 Journal of Bone and Mineral Research No. 7, pp. 1679-1687 (Jul. 2013).

Taton, Grzegorz et al., "Combining Areal DXA Bone Mineral Density and Vertebrae Postero-Anterior Width Improves the Prediction of Vertebral Strength," 42 Skeletal Radiol, pp. 1717-1725 (Oct. 2013).

\* cited by examiner ial Patent Application No. 61/927,302 filed Jan. 14, 2014, the entire disclosure of which is incorporated herein by reference. This application also claims priority to U.S. Provisional Patent Application No. 61/927,715 filed Jan. 15, 2014, the entire disclosure of which is incorporated herein by reference. This application also claims priority to U.S. Provisional Patent Application No. 61/928,591 filed Jan. 17, 2014, the entire disclosure of which is incorporated herein by reference.

METHOD AND SYSTEM FOR BONE FRACTURE RISK ASSESSMENT

CROSS-REFERENCE TO RELATED APPLICATIONS

This application claims priority to U.S. Provisional Patent Application No. 61/927,302 filed Jan. 14, 2014, the entire disclosure of which is incorporated herein by reference. This application also claims priority to U.S. Provisional Patent Application No. 61/927,715 filed Jan. 15, 2014, the entire disclosure of which is incorporated herein by reference. This application also claims priority to U.S. Provisional Patent Application No. 61/928,591 filed Jan. 17, 2014, the entire disclosure of which is incorporated herein by reference.

BACKGROUND OF THE INVENTION a. Field of the Invention

This invention relates to assessment of bone fracture risk and, in particular, to a method and system for quantitatively evaluating bone fracture risk in a living being that implement an improved index of bone fracture risk.

b. Background Art

Bone tissue breaks down and rebuilds within living beings. In humans, bone tissue initially forms faster than it is lost when a human is young. At a certain age, however, humans begin to lose bone tissue at a greater rate than it is replenished. As bone mass diminishes, bones have a greater risk of fracture. The risk is particularly acute in individuals who have osteopenia, or low bone mass, or suffer from the bone thinning disease osteoporosis.

Because bone fractures can negatively impact overall health, methods and systems have been developed to evaluate bone fracture risk with a particular emphasis on individuals having osteopenia or osteoporosis. Conventional methods and systems rely on bone mass and body mass index (BMI). The use of BMI, however, does not appropriately account for the nature of an individual's height, weight and bone mass.

The inventors herein have recognized a need for a method and system for quantitatively evaluating bone fracture risk in a living being that will overcome one or more of the above-identified deficiencies.

BRIEF SUMMARY OF THE INVENTION

A method and system for quantitatively evaluating bone fracture risk in a living being are provided. In particular, a method and system are provided that implements an improved index of bone fracture risk.

A method for quantitatively evaluating bone fracture risk in a living being in accordance with one embodiment of the invention includes the step of acquiring values for a height H, a weight W, and a bone mineral density BMD of the living being. The method further includes the step of calculating a quantitative bone fracture risk index QI associated with the living being in accordance with the formula $QI=H^{\alpha}*W^{\beta}/BMD^{\gamma}$ where $\alpha$, $\beta$, and $\gamma$ are constants selected based on previously obtained data indicative of bone fracture risk, the index indicative of a degree of bone fracture risk in the living being.

A system for quantitatively evaluating bone fracture risk in a living being in accordance with one embodiment of the invention includes a computing device configured to acquire values for a height H, a weight W, and a bone mineral density BMD of the living being. The computing device is further configured to calculate a quantitative bone fracture risk index QI associated with the living being in accordance with the formula $QI=H^{\alpha}*W^{\beta}/BMD^{\gamma}$ where $\alpha$, $\beta$, and $\gamma$ are constants selected based on previously obtained data indicative of bone fracture risk, the index indicative of a degree of bone fracture risk in the living being.

A method for quantitatively evaluating bone fracture risk in a living being in accordance with another embodiment of the invention includes the step of acquiring values for a size and a bone mineral density BMD of a bone of the living being. The method further includes the step of calculating a bone strength index BSI associated with the living being by dividing the bone mineral density by the size, the index indicative of a degree of bone fracture risk in the living being.

A system for quantitatively evaluating bone fracture risk in a living being in accordance with another embodiment of the invention includes a computing device configured to acquire values for a size and a bone mineral density BMD of a bone in the living being. The computing device is further configured to calculate a bone strength index BSI associated with the living being in by dividing the bone mineral density BMD by the size, the index indicative of a degree of bone fracture risk in the living being.

A method and system for quantitatively evaluating bone fracture risk in a living being in accordance with the present teachings are advantageous relative to conventional methods and systems because the inventive methods and systems better account for the nature of height, weight and bone mass in a living being.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Figure 1:
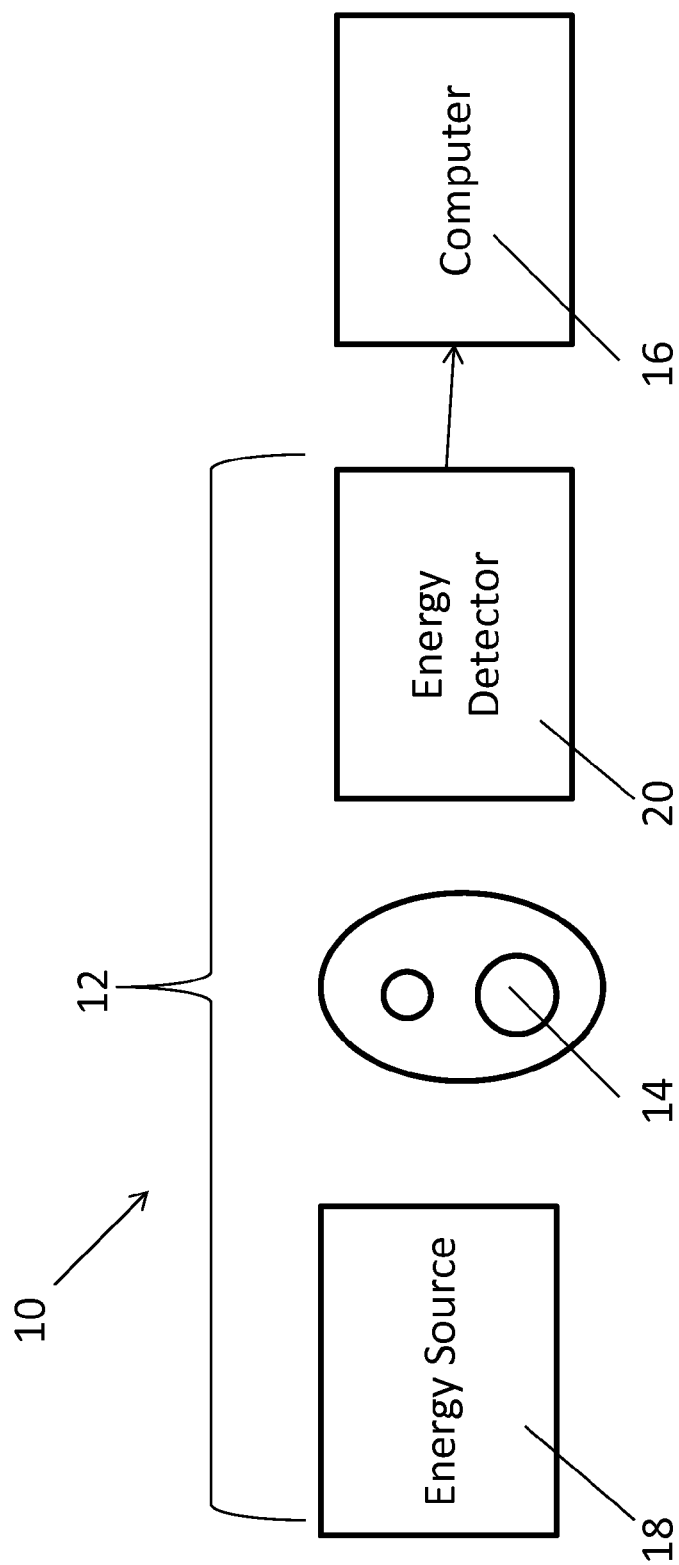
FIG. 1 is a diagrammatic view of a system for quantitatively evaluating bone fracture risk in accordance with one embodiment of the present teachings.

Referring now to the drawings wherein like reference numerals are used to identify identical components in the various views, FIG. 1 illustrates one embodiment of an system 10 for quantitatively evaluating bone fracture risk in a living being in accordance with the present teachings. System 10 may include a device 12 of measuring bone mineral density in a bone 14 of a living being and a computing device 16.

Device 12 is provided to measure bone mineral density (BMD) of bone 14. Device 12 may include an energy source 18 and an energy detector 20 disposed on opposite sides of bone 14. Device 12 may comprise, for example, a dual energy x-ray absorptiometry (DXA or DEXA) machine capable of generating areal BMD in grams/centimeter$^2$ or a bone mineral content in grams. In certain embodiments, device 12 comprises the QDR 4500 DXA machine offered for sale by Hologic Corp. of Bedford, Mass. Alternatively, device 12 may comprise a quantitative computed tomography (QCT) device capable of generating volumetric BMD in grams/centimeter$^3$. It should be understood that other devices could be used to obtain BMD including single photon absorptiometry (SPA) devices, dual photon absorptiometry (DPA) devices, high-resolution peripheral quantitative computed tomography (HR-pQCT) devices such as the device offered for sale under the trademark XtremeCT by Scanco Medical of Bruttisellen, Switzerland, plain or digital radiographic devices or ultrasound devices.

Bone 14 comprises a radius bone in the illustrated embodiment. It should be understood, however, that BMD can be measured in a variety of bones including the ulna, femur, hip or vertebra.

Computing device 16 calculates an index indicative of bone fracture risk. Computing device 16 may include a central processing unit (CPU), memory and an input/output (I/O) interface through which device 16 may receive a plurality of input signals including, for example, measurements of an individual's height and weight, bone mineral density, or a size associate with a bone and generate a plurality of output signals including an indicator of bone fracture risk. Computing device 16 may be programmed to execute a sequence of instructions (i.e. software) to perform certain steps of a method for quantitatively evaluating bone fracture risk in a living being.

Figure 2:
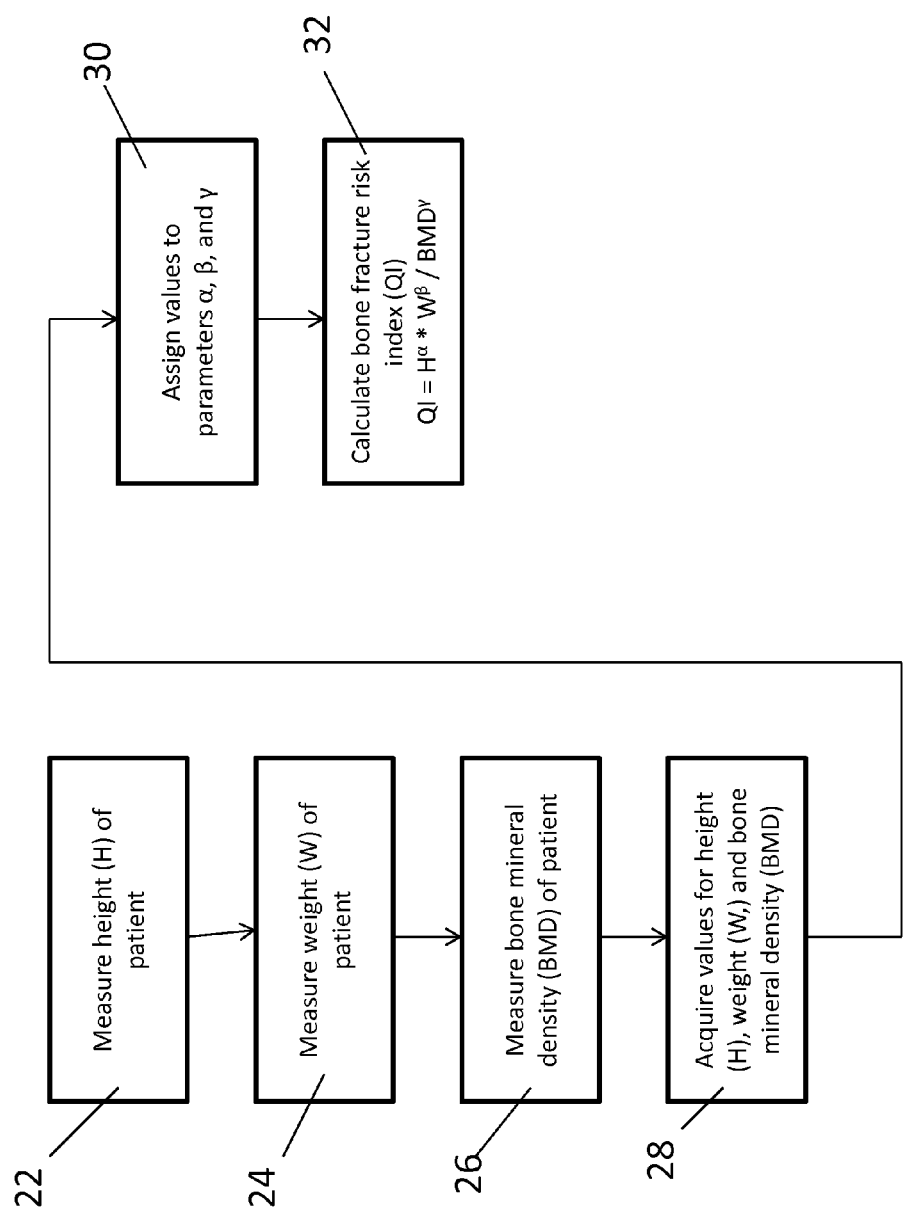
FIG. 2 is a flow chart diagram of a method for quantitatively evaluating bone fracture risk in accordance with one embodiment of the present teachings.

Referring to FIG. 2, in accordance with one embodiment of the invention a method for quantitatively evaluating bone fracture risk in a living being may being with the steps 22, 24, 26 of measuring the height H, weight W, and bone mineral density BMD of the living being. Height H and weight W may be measured before or during a procedure in a number of ways known in the art. BMD may be measured by device 12.

The method may continue with the step 28 of acquiring the height H, weight W and BMD. Computing device 16 may acquire or receive the height H and/or weight W through conventional input devices over a wired or wireless network. For example, a user may enter a manually measured height and/or weight using a keyboard or other input device. Alternatively, height and weight measured by measurement devices (e.g., a digital scale) can be directly transferred to computing device 16. Device 16 may acquire or receive a measurement of bone mineral density BMD directly from device 12 over a wired or wireless network.

The method may further include the step 30 of assigning values to certain parameters α, β, and γ (use of which is discussed hereinbelow) based on one or more characteristics of the patient. For example, values of α, β, and γ may vary based, in part, on gender, age or other characteristics of a patient. Information regarding the patient is used to assign values for α, β, and γ based on previously obtained data indicative of fracture risk for a comparable patient population. This information may be stored in a data structure in a memory of computing device 16 or a remote memory accessible by computing device 16 and may be obtained from the data structure responsive to inputs indicative of characteristics of the patient.

The method may continue with the step 32 of calculating a quantitative bone fracture risk index QI associated with the living being in accordance with the formula $$QI = H^\alpha * W^\beta / BMD^\gamma$$

where H, W and BMD equal the height, weight and bone mineral density of the patient and α, β, and γ are constants selected based on previously obtained data indicative of bone fracture risk as discussed in step 30 above. Significantly, each of α, β, and γ are greater than zero. Each of α, β, and γ are also preferably less than 4 and in one embodiment α equals 1.5, β equals 0.5, and γ equals 2.0. The inventors have found that the bone fracture risk index QI provides an improved assessment of bone fracture risk relative to conventional methods and systems which rely on body mass index (BMI) because BMI fails to account for the nature of an individual's height, weight and bone mass.

Figure 3:
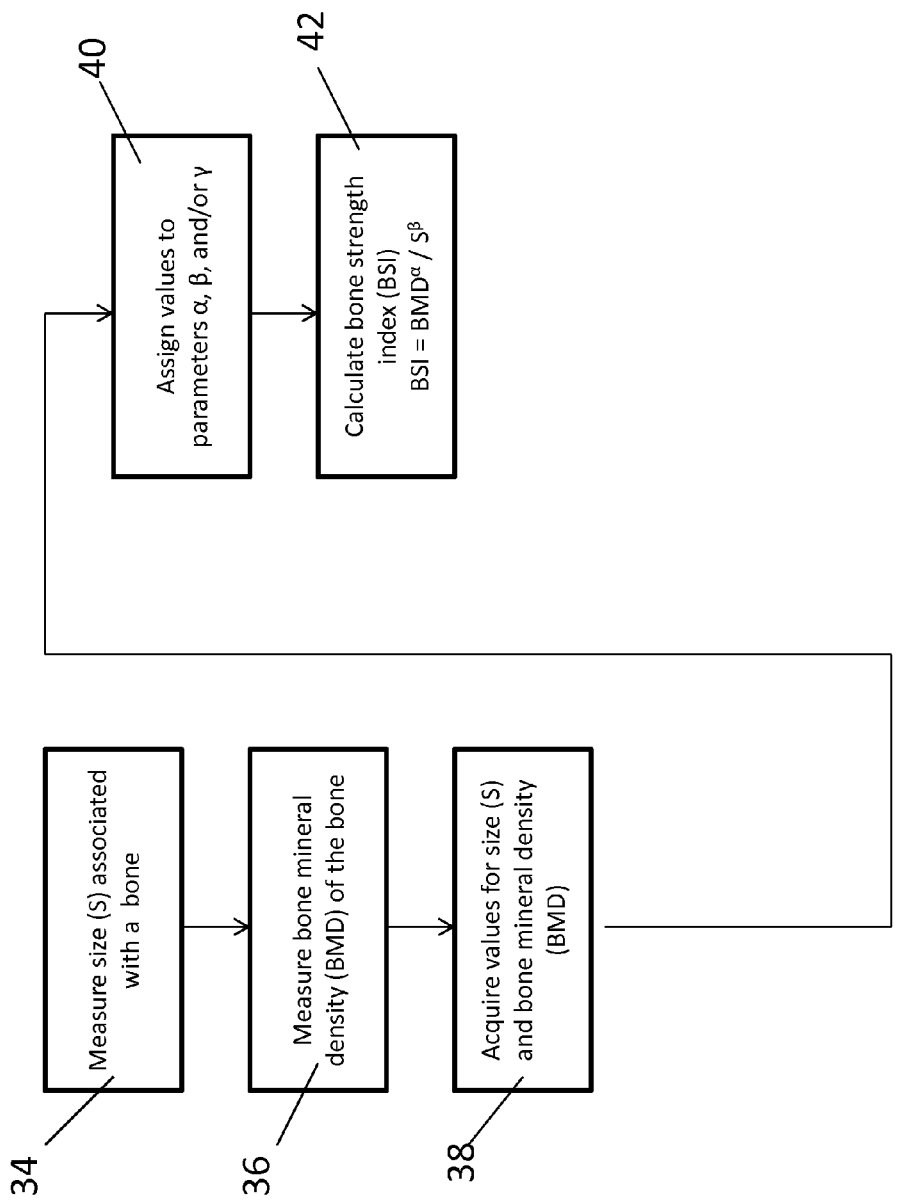
FIG. 3 is a flow chart diagram of a method for quantitatively evaluating bone fracture risk in accordance with another embodiment of the present teachings.

Referring now to FIG. 3, in accordance with another embodiment of the invention, a method for quantitatively evaluating bone fracture risk in a living being may begin with the steps 34, 36 of measuring a size S and bone mineral density BMD for one or more bones in a living being. In accordance with one embodiment of the invention, the bone comprises a radius bone. It should be understood, however, that the invention may be applied to other bones in a living being such as an ulna, femur, hip or vertebra. In accordance with one embodiment of the invention, the measured size S of the bone has one dimension. For example, the size S may comprise the width w of the bone at a particular location. In one embodiment, the width w is measured at the ultra-distal region of interest of the radius. Because the ultra-distal region of interest extends over a length of the radius, the width w may comprise a minimum or maximum width of the radius in this region or an average width $w_{avg}$ over the length of the ultra distal region of the radius. In accordance with another embodiment of the invention, the measured size S of the bone has two dimensions. For example, the size S may comprise an area A of the radius bone at the ultra distal region such as the width w of the bone multiplied by the thickness d of the bone. Each of these values may again be averaged over a length of the bone. Device 12 may be used to measure both the selected size of the bone at a particular location or region of interest and the BMD at the same location or region of interest.

The method may continue with the step of 38 of acquiring values for the size S and bone mineral density BMD of a bone, such as the radius bone, of a living being. Computing device 16 may acquire or receive the size S (or sizes) and bone mineral density BMD directly from device 12 over a wired or wireless network.

The method may further include the step 40 of assigning values to one or more parameters α, β, and γ (use of which is discussed hereinbelow) based on one or more characteristics of the patient. For example, values of α, β, and γ may vary based, in part, on gender, age or other characteristics of a patient. Information regarding the patient is used to assign values for α, β, and γ based on previously obtained data indicative of fracture risk for a comparable patient population. This information may be stored in a data structure in a memory of computing device 16 or a remote memory accessible by computing device 16 and may be obtained from the data structure responsive to inputs indicative of characteristics of the patient.

The method may continue with the step 42 of calculating a bone strength index BSI associated with the living being by dividing the bone mineral density (BMD) by the selected size S in accordance with the formula $$BSI = BMD^\alpha / S^\beta$$

where BMD and S equal the bone mineral density and a sized associated with a bone and α and β are constants selected based on previously obtained data indicative of bone fracture risk as discussed in step 40 above. Significantly each of α and β are again greater than zero. In one embodiment, the size S comprises a width w of a bone and, in particular, a width w of the ultra distal region of the radius bone and the bone strength index BSI is calculated in accordance with the formula $$BSI=BMD^\alpha/w^\beta$$

where $\alpha$ equals 1.0 and $\beta$ equals 3.0 (in an alternate embodiment $\alpha$ equals 2.0 and $\beta$ equals 3.0). In another embodiment, the size S comprises an area A of a bone and, in particular, the area A of the ultra distal region of the radius bone and the bone strength index BSI is calculated in accordance with the formula $$BSI=BMD^\alpha/A^\beta$$

where $\alpha$ equals 1.0 and $\beta$ equals 4.0 (in an alternate embodiment $\alpha$ equals 3.0 and $\beta$ equals 7.0). In a more specific embodiment, the area A is determined based on the width w and thickness d of the bone and, in particular, the ultra distal region of the radius bone and the bone strength index BSI is calculated in accordance with the formula $$BSI=BMD^\alpha/d^\beta*w^\gamma$$

where $\alpha$ equals 1.0 and $\beta$ equals 2.0 and $\gamma=2.0$ (in an alternate embodiment $\alpha$ equals 2.0 and $\beta$ equals 2.0 and $\gamma$ equals 2.0).

A method and system for quantitatively evaluating bone fracture risk in a living being in accordance with the present teachings are advantageous relative to conventional methods and systems because the inventive methods and systems better account for the nature of height, weight and bone mass in a living being.

While the invention has been shown and described with reference to one or more particular embodiments thereof, it will be understood by those of skill in the art that various changes and modifications can be made without departing from the spirit and scope of the invention.

We claim:

1. A method for quantitatively evaluating bone fracture risk in a living being, comprising the steps of:
    acquiring values for a height H, a weight W, and a bone mineral density BMD of said living being; and,
    calculating a quantitative bone fracture risk index QI associated with said living being in accordance with the formula $$QI=H^\alpha*W^\beta/BMD^\gamma$$

where $\alpha$, $\beta$, and $\gamma$ are constants selected based on previously obtained data indicative of bone fracture risk, said index indicative of a degree of bone fracture risk in said living being.

2. The method of claim 1 wherein $\alpha$, $\beta$, and $\gamma$ are all greater than zero.

3. The method of claim 2 wherein $\alpha$, $\beta$, and $\gamma$ are all less than four.

4. The method of claim 3 wherein $\alpha=1.5$, $\beta=0.5$ and $\gamma=2$.

5. The method of claim 1 wherein said acquiring step includes the substep of measuring said bone mineral density using dual energy x-ray absorptiometry.

6. The method of claim 1 wherein said acquiring step includes the sub step of measuring said bone mineral density using quantitative computed tomography.

7. A system for quantitatively evaluating bone fracture risk in a living being, comprising:
    a computing device configured to
    acquire values for a height H, a weight W, and a bone mineral density BMD of said living being; and,
    calculate a quantitative bone fracture risk index QI associated with said living being in accordance with the formula $$QI=H^\alpha*W^\beta/BMD^\gamma$$

where $\alpha$, $\beta$, and $\gamma$ are constants selected based on previously obtained data indicative of bone fracture risk, said index indicative of a degree of bone fracture risk in said living being.

8. A method for quantitatively evaluating bone fracture risk in a living being, comprising the steps of:
    acquiring values for a size of a bone and a bone mineral density BMD of said bone of said living being; and,
    calculating a bone strength index BSI associated with said living being by dividing said bone mineral density by said size, said index indicative of a degree of bone fracture risk in said living being.

9. The method of claim 8 wherein said size comprises a width w of said bone and said bone strength index BSI is calculated in accordance with the formula $$BSI=BMD^\alpha/w^\beta$$

where $\alpha$ and $\beta$ are constants selected based on previously obtained data indicative of bone fracture risk.

10. The method of claim 8 wherein said size comprises an area A of said bone and said bone strength index BSI is calculated in accordance with the formula $$BSI=BMD^\alpha/A^\beta$$

where $\alpha$ and $\beta$ are constants selected based on previously obtained data indicative of bone fracture risk.

11. The method of claim 8 wherein said bone comprises a radius bone.

12. A system for quantitatively evaluating bone fracture risk in a living being, comprising:
    a computing device configured to
    acquire values for a size of a bone and a bone mineral density BMD of said bone in said living being; and,
    calculate a bone strength index BSI associated with said living being in by dividing said bone mineral density BMD by said size, said index indicative of a degree of bone fracture risk in said living being.

* * * * *